(12) United States Patent
Puttaswamy et al.

(10) Patent No.: US 11,537,201 B1
(45) Date of Patent: Dec. 27, 2022

(54) EYE TRACKING IMAGER WITH GATED DETECTORS RECEIVING A SPECULAR REFLECTION

(71) Applicant: MICROSOFT TECHNOLOGY LICENSING, LLC, Redmond, WA (US)

(72) Inventors: Niranjan Achugundla Puttaswamy, San Jose, CA (US); Gregory Theodore Gibson, Duvall, WA (US); Jeffrey Neil Margolis, Seattle, WA (US); John Allen Tardif, Bellevue, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 17/364,878

(22) Filed: Jun. 30, 2021

(51) Int. Cl.
| | |
|---|---|
| *G06F 3/01* | (2006.01) |
| *G06T 5/20* | (2006.01) |
| *H04N 5/378* | (2011.01) |
| *G06T 7/73* | (2017.01) |
| *G06T 7/246* | (2017.01) |
| *G02B 5/20* | (2006.01) |
| *A61B 3/14* | (2006.01) |

(Continued)

(52) U.S. Cl.
CPC ............ *G06F 3/013* (2013.01); *G06T 5/20* (2013.01); *G06T 7/248* (2017.01); *G06T 7/74* (2017.01); *H04N 5/378* (2013.01); *A61B 3/14* (2013.01); *G02B 5/20* (2013.01); *G06T 2207/30201* (2013.01); *G06V 40/19* (2022.01); *G06V 40/197* (2022.01)

(58) Field of Classification Search
None
See application file for complete search history.

(56) References Cited

U.S. PATENT DOCUMENTS

| | | | |
|---|---|---|---|
| 10,551,914 B2 | 2/2020 | Price et al. | |
| 10,627,899 B2 | 4/2020 | Price et al. | |
| 10,897,586 B2 * | 1/2021 | Liu | ............ H04N 5/37452 |

(Continued)

OTHER PUBLICATIONS

"International Search Report and Written Opinion Issued in PCT Application No. PCT/US2022/031664", dated Sep. 20, 2022, 13 Pages.

*Primary Examiner* — Talha M Nawaz
(74) *Attorney, Agent, or Firm* — Scott Y. Shigeta; Newport IP, LLC

(57) ABSTRACT

Technologies are described herein for an eye tracking that may be employed by devices and systems such as head mount display (HMD) devices. Light that is reflected from a user's eye may be specular or scattered. The specular light has an intensity or magnitude that may saturate the electronics. The presently disclosed techniques mitigate saturation by generating detected signals from an optical detector, evaluating the signal levels for the detected signal, and selectively gating the detected signals that have saturated. The remaining scattered signals can be combined to achieve a combined signal that can be converted into a digital signal without saturating the electronics, which can then be processed to form an image of the eye for identification purposes, for tracking eye movement, and for other uses. The described technologies provide a clear image without ambient light reflections or specular light interfering with the image.

20 Claims, 8 Drawing Sheets

(51) Int. Cl.
 *G06V 40/19* (2022.01)
 *G06V 40/18* (2022.01)

(56) References Cited

U.S. PATENT DOCUMENTS

2018/0314325 A1    11/2018  Gibson et al.
2020/0007798 A1*   1/2020   Liu ........................... G01J 1/44
2021/0243390 A1*   8/2021   Liu ........................ H04N 5/353

\* cited by examiner

EYE TRACKING IMAGER WITH GATED DETECTORS RECEIVING A SPECULAR REFLECTION

BACKGROUND

Near-Eye-Display (NED) systems are designed to generate computer-generated images ("CG images") that are observable in a user's field of view. In one example, an augmented-reality (AR) system generates one or more hologram images that are rendered in the user's line of sight, where the hologram images are overlaid or combined with other objects present in the real world. In another example, a virtual-reality (VR) system creates a user's entire view such that the real world is completely obstructed by a virtual world.

The NED systems may often be referred to as a head-mounted display, hereinafter "HMD," since the NED system is typically worn as a headset that is located on the user's head about their eyes. An HMD can include cameras or video devices for capturing the real-world scenes and objects, as well as other devices such as gyroscopic sensors to sense motion and movement of the user's head. As a user moves their head during a session, the various sensors can detect motion and rendered the correct images and environment so that the user may be provided with a proper perspective and view of the virtual objects. In some instances, the HMD system may include additional devices to track the motion of a user's eye. By tracking motion of the eye, the HMD can determine the appropriate images to render based on the direction and focus of the user's gaze.

The disclosure made herein is presented with respect to these and other considerations.

SUMMARY

Technologies are described herein for an eye tracking that may be employed by devices and systems such as head mount display (HMD) devices. Light that is reflected from a user's eye may be specular or scattered. The specular light has an intensity or magnitude that may saturate the electronics. The presently disclosed techniques mitigate saturation by generating detected signals from an optical detector, evaluating the signal levels for the detected signal, and selectively gating the detected signals that have saturated. The remaining scattered signals can be combined to achieve a combined signal that can be converted into a digital signal without saturating the electronics, which can then be processed to form an image of the eye for identification purposes, for tracking eye movement, and other for uses. The described technologies provide a clear image without ambient light reflections or specular light interfering with the image.

It should be appreciated that the above-described subject matter may also be implemented as part of an apparatus, system, or as part of an article of manufacture. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

BRIEF DESCRIPTION OF THE DRAWINGS

The Detailed Description is described with reference to the accompanying figures. References made to individual items of a plurality of items can use a reference number with a letter of a sequence of letters to refer to each individual item. Generic references to the items may use the specific reference number without the sequence of letters.

DETAILED DESCRIPTION

Figure 1:
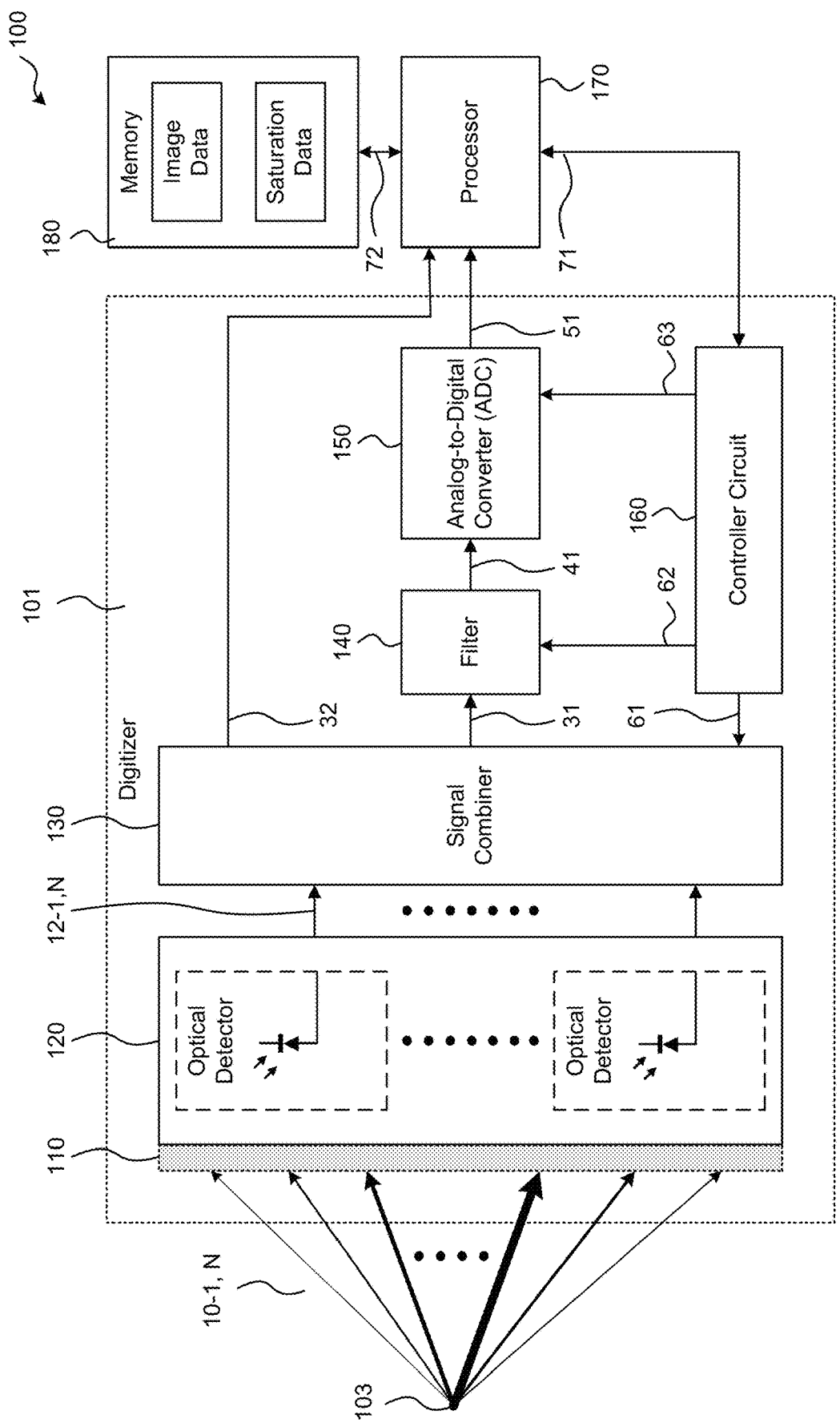
FIG. 1 shows a schematic diagram of an example imager system.

In the following detailed description, reference is made to the accompanied drawings, which form a part hereof, and which is shown by way of illustration, specific example configurations of which the concepts can be practiced. These configurations are described in sufficient detail to enable those skilled in the art to practice the techniques disclosed herein, and it is to be understood that other configurations can be utilized, and other changes may be made, without departing from the spirit or scope of the presented concepts. The following detailed description is, therefore, not to be taken in a limiting sense, and the scope of the presented concepts is defined only by the appended claims.

Throughout the specification and claims, the following terms take the meanings explicitly associated herein, unless the context clearly dictates otherwise. The meaning of "a," "an," and "the" includes plural reference, the meaning of "in" includes "in" and "on." The term "connected" means a direct electrical connection between the items connected, without any intermediate devices. The term "coupled" means a direct electrical connection between the items connected, or an indirect connection through one or more passive or active intermediary devices and/or components. The terms "circuit" and "component" means either a single component or a multiplicity of components, either active and/or passive, that are coupled to provide a desired function. The term "signal" means at least a power, current, voltage, or data signal.

Technologies are described herein for an eye tracking that may be employed by devices and systems such as head mount display (HMD) devices. Light that is reflected from a user's eye may be specular or scattered. The specular light has an intensity or magnitude that may saturate the electronics, which may occlude certain features of the eye that could be used for user authentication. The presently disclosed techniques mitigate saturation by generating detected signals from an optical detector, evaluating the signal levels for the detected signal, and selectively gating the detected signals that have saturated. The remaining scattered signals can be combined to achieve a combined signal that can be converted into a digital signal without saturating the electronics, which can then be processed for a number of uses such as tracking eye movement, capturing a clear view of features for a user's eye that may be used for authentication, etc.

HMD devices often include multiple lasers that each emit a beam of laser light corresponding to a different color (e.g., Red, Green, Blue), and one or more mirror devices that direct each of the beams of laser light into the user's field of view. The mirror devices, which are typically implemented as a micro electromechanical systems (MEMs) based devices, direct and/or deflect the beams to scan across a region of the user's eye. Through this scanning operation, a MEMs-based scanner device is able to render an image that is viewable to the user.

In addition to a color image that is directed to the user's eye as a drawn image by one or more lasers, the HMD device may also include a laser that emits an infrared (IR) light beam (or light wave). The infrared light beam may be deflected or directed to the user's eye by a MEMS based mirror device. In some examples, the same MEMS mirror device as one of the color lasers may be used to deflect or direct the IR light beam to the user's eye.

An IR light beam may be used to track the motion of the user's eye as will be further described below. However, any other wavelength of light may also be used to track the user's eye. For example, one or more of a red (R) laser light, a green (G) laser light, a blue (B) laser light, or various combinations thereof may be used to track the user's eye. Additionally, an infrared laser light may be used in combination with one or more of the red laser light, the green laser light, and/or the blue laser light, without departing from the spirit of the present disclosure. For simplicity, the remaining disclosure will refer to the infrared light beam being used for eye-motion tracking, but the disclosure is not so limited.

Once an infrared light wave strikes an object such as the user's eye, light will be reflected and scattered by the surface, referred to as a specular or a scattered reflection. For a specular reflection, the reflected ray of light will have an angle of reflection ($\theta_r$) that is the same as the incident angle ($\theta_i$), meaning $\theta_r = \theta_i$; while for a scattered reflection the reflected ray of light will have a different angle of reflection ($\theta_r$) from the incident angle ($\theta_i$), meaning $\theta_r \neq \theta_i$. The specular reflection corresponds to the "glint" of the user's eye, while the scatter reflections correspond to the user's iris information. As a result, these reflections can also be used to authenticate the user's iris.

Due to the properties of the surface of a user's eye, multiple reflections may be generated at the same time from one incident light beam. Each of these reflections will have a different reflection angle, where the intensity (or amplitude) of a specular reflection will be higher than the intensity of any of the scattered reflection. These reflections can be captured and analyzed by photosensitive devices, as will be further described below.

FIG. 1 shows a schematic diagram of an example eye-tracking imager system 100 that is arranged in accordance with aspects of the presently disclosed technology. System 100 includes a digitizer 101, a processor 170, and a memory 180.

Digitizer 101 is configured to receive one or more reflected light beams, 10-1 to 10-N, from an object 103. The reflected light beams, 10-1 through 10-N, may correspond to direct reflections from an object or indirect reflections from the object. Indirect reflections may be provided by other optical devices, including but not limited to optical waveguides, lenses, convex or concave lenses, collimators, prisms, mirrors, MEMS, filters, etc.). In various examples described herein, the object that is the source of reflections may correspond to a user's eye.

The digitizer 103 may be used to capture the specular and scattered reflections from the object (or user's eye) and to generate an electrical response. The electrical response can be a digital signal 51, which may then be processed by processor 170 to generate an image. Processor 170 can interact with memory 180 via a communication bus 72. In some examples, processor 170 may include memory 180 as either a separate memory or an onboard memory, which may be configured to store image data for each of the pixels from the image(s).

In one example, processor 170 captures image data from digital signal 51, wherein the captured image data is time stamped and stored in memory 180. The captured image data can be correlated with the x, y pixel positions based on time, since the scan angle of the mirrors correspond to specific pixel positions. Thus, an image can be formed by correlation of the captured image data and the corresponding x,y position based on the time stamp.

The processor 170 may be a controller, a microcontroller, a microprocessor, a digital signal processor, or any other appropriate processor that may be implemented as an integrated or discrete solution, or a combination thereof. An example processor 170 may also be implemented as a system-on-a-chip (SOIC), an application specific integrated circuit (ASIC), a hybrid circuit, or some combination thereof.

The digitizer 103 may be used to generate an initial image of a user's eye from a digital signal 51 that is output from the digitizer 103. Additionally, multiple eye images may be generated from the digital signal 51, spanning across a time period. The digital signal(s) 151 for each individual image corresponds to a position of the user's eye at a specific point in time. The differences between each image can be evaluated (e.g., by processor 170) to determine how the user's eye moves from one image to the next, tracking the direction of gaze and/or movement of the eye position over time.

The digitizer 101 of FIG. 1 includes an optical filter 110, an optical detector 120, a signal combiner 130, an analog filter 140, an analog-to-digital converter (ADC) 150, and a controller circuit 160. The optical filter 110 is positioned between the optical detector 120 and the reflected light beams 10-1 to 10-N. Responsive to the reflected lights beams, 12-1 to 12-N, the optical detector 120 is configured to generate analog detection signals 12-1 to 12-N. Signal combiner 130 is configured to receive the analog detection signals 12-1 to 12-N and generate a combined analog signal 31, which corresponds to a summation of one or more of the analog detection signals 12-1 to 12-N. The combined analog signal 31 is received by the analog filter 140, which responsively generates a filtered analog signal 41. The filtered analog signal 41 is received by the analog-to-digital converter 150, which responsively generates the digital signal 51.

Optical filter 110 is an optional device that may be employed for wavelength or spatial filtering of optical signals received by the optical detector 120. This filter can be configured to filter out light with wavelengths that are different from the incident beam (e.g. the wavelength of the beam that is incident on object 103). In one example, the optical filter 110 can be used to block undesired ambient light, while allowing the reflected light from the object 103 to pass through the optical filter 110. In another example, the optical filter 110 can be configured to block out (or alternatively pass light) in the red, green, and/or blue light spectrums. In yet another example, the optical filter 110 may be configured to block light waves with wavelengths in the visible spectrum. In still other examples, the optical filter 110 may be configured to block light (or alternatively pass light) with a wavelength in a specific portion of the infrared wavelength spectrum (or any other spectrum). In yet still other examples, the optical filter 110 may be configured to block or pass light with a specific polarization.

Optical detector 120 is a sensor device that is configured to generate multiple (N) electrical signals 12-1 to 12-N, or analog detection signals, which result from light being detected as incident on the optical detector 120. Optical detector 120 is a photo-multiplier type of device that includes multiple photodiode circuits, each one generating a signal responsive to light incident thereon. The photodiode circuits are photosensitive PN junction devices that can be built on a silicon substrate, where each PN junction generates an electrical signal in response to photons that are incident thereon. In some examples, the photodiode circuits include avalanche type photodiodes, while in other examples the photodiode circuits include PIN type photodiodes.

The signal combiner 130 is configured to receive the electrical signals 12-1 to 12-N from the optical detector 120, and combine the signals into a single analog output, combined analog signal 31. The signal combiner 130 includes circuitry and/or logic that favors non-saturated signals over saturated signals, given that the non-saturated signals contain useful information, while saturated signals contain less useful information. As such, the circuits and/or logic of the signal combiner is configured to evaluate adjacent pairs of detection signals to determine if either of the adjacent pairs of signals have saturated, and promotes the non-saturated signal for summation with the other signals.

In some examples, the signal combiner 130 may provide one or more digital saturation detection signals 32 to the processor 170, where digital signal 32 indicates whether saturation occurs in the optical detector 120. Processor 170 may capture the digital saturation detection signals 32 and store saturation data in memory 180. The saturation data may further include a time stamp that can be correlated with other characteristics of the image generation (e.g., a time and position of a scanning mirror can be correlated to an image of the eye at a particular scan angle).

Analog Filter 140 is an optional device that may be any variety of analog filter that may be employed to filter the combined analog signal 31 from the signal combiner 130 prior to sampling the electrical response with ADC 150. The analog filter may be a high-pass filter, a low-pass filter, a band-pass filter, a phase-shape filter, or any combination thereof. The filter(s) may be employed to effectively reduce the signal-to-noise ratio to improves the output of the ADC 150. In some examples, the analog filter 140 may include a passive circuit (e.g. without gain), while in other examples the analog filter 140 may include an active circuit (e.g. with gain).

ADC 150 is an analog-to-digital converter that is configured to sample the electrical response from an optical detector 120, via the combined analog signal 31 from the signal combiner 130. ADC 150 may sample the combined analog signal 31 at a predetermined frequency. As previously described, an optional analog filter 140 may be employed to filter the optical sensor's electrical response before the ADC samples, thereby reducing the signal to noise ratio and improves the output of the ADC. Also, a gain block may be employed to gain scale the signal before conversion by ADC 150 to improve the quantization and/or linearity of the ADC. The described gain block may be separate from the filter, included in the filter, or incorporated in the ADC 150. In some further examples, multiple optical detectors 120 may be employed, each with a corresponding signal combiner 130 and ADC 150.

The controller circuit 160 is configured to receive one or more configuration signals from the processor 170 via a communication interface 71, which may be either an analog configuration signal or a digital configuration signal (e.g., data). In response to the one or more configuration signals, the controller circuit 160 is configured to generate one or more control signals for the signal combiner 130, the analog filter 140, and the ADC 150. As will be described later, one control signal, e.g., 61, may be utilized to configure threshold voltage settings in the signal combiner 130. Another control signal, e.g. 62, may be utilized to adjust filter or gain coefficients for analog filter 140. Still another control signal, e.g. 63, may be utilized to control ADC 150 (e.g., start/end/run calibration of the ADC, adjust/select a reference value for the ADC, clock frequency or duty cycle of clock signals, adjust gain or linearity of the ADC, etc.).

The intensity of a specular reflection is higher than the intensity of a diffuse/scattered reflected infrared light waves. In FIG. 1, intensity is shown by the varying thickness of the weighted lines. The thinnest lines have the lowest intensity, while the thickest lines have the highest intensity.

As previously stated, an incident laser beam on an object (such as a user's eye) will result in specular and scattered reflections that can be captured by the digitizer 103 to generate an electrical response. However, there is a high likelihood that a reflection from the cornea of a user will result a large specular reflection, where a large percentage of the incident laser power will reflect from the object and become incident on the optical detector 120. This large specular reflection may result in an undesirable saturation of the optical detector 120 and/or the signal processing electronics. For example, the signals resulting from the specular reflections can exceed the dynamic range of the optical sensors or the signal processing electronics, which results in a saturated area of the image. Information in these saturated areas is essentially lost, since the saturated areas offer no information.

The signal combiner 130 described herein is configured to evaluate the output of the optical detector 120 output and gate the detector signals that are likely to saturate the signal electronics. Saturation is avoided and the overall signals can be processed for improved images without loss of information. As will be described herein, the signal combiner 130 includes selection logic that automatically preserves the intensity level in regions that have been gated off due to the specular reflections. A continuous greyscale image may be formed without areas that would have been saturated by the specular reflections. The image data is captured by processor 170 capturing digital signal 31, which is output from ADC 150, and storing the collection of samples in memory 180.

In addition to detection, the saturation information about the optical detector 120 can be utilized to assist in image capture and detection of glints. The location of a glint in an image may be correlated to the position of the mirror at the time where a spectral reflection is observed. For example, a spectral reflection may be identified when a optical detector 120 saturates at a particular time, which is captured as digital saturation detection signal 32 along with a time stamp of the capture; and the mirror position of the scanner at that same time provides angle information. For this example, an image may be formed two ways: a first image may be formed from a collection of digital signal 51 and time stamped from ADC 150, and a second image may be formed from a collection of time stamped digital saturation detection signals 32. The first image may correspond to the collection of pixel information for an unsaturated image (e.g. from signal 51); while the second image may correspond to the collection of saturation detections (e.g., from signal 32). The time stamped saturation detection signals may thus correspond to mask, where the mask highlights common centroid saturation regions in the unsaturated image. The combination of the two images can be used to closely track the eye position.

In other examples, the described images may be used to track features of the eye such as in a user authentication system, where features of the user's eye may be captured and stored for authentication purposes. Since specular light has an intensity or magnitude that may saturate the electronics, such a saturation may occlude certain features of the eye that could be used for the user authentication. The presently disclosed techniques provide the benefit of gating off detectors that would occlude those features, and thus a clear image is provided without ambient light reflections or specular light interfering with the image.

Figure 2:
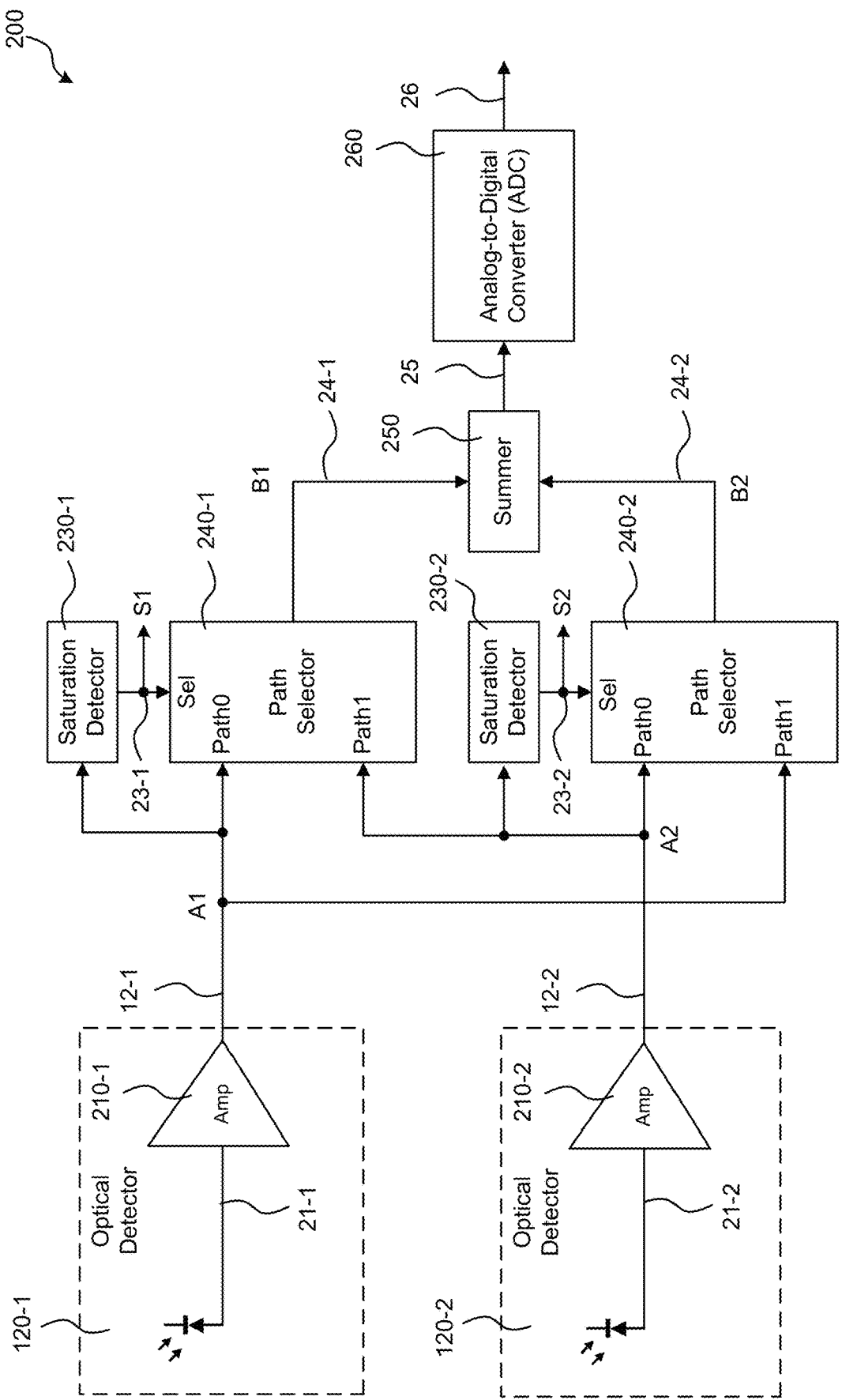
FIG. 2 shows a schematic diagram of another example imager system.

FIG. 2 shows a schematic diagram of another example imager system 200 that is arranged in accordance with the presently disclosed techniques. System 200 includes optical detector circuits 120-1 and 120-2, saturation detectors 230-1 and 230-2, path selectors 240-1 and 240-2, summer 250, and ADC 260.

Optical detector circuits 120-1 and 120-2 are photodetector circuits that are each configured to generate a respective one of analog detection signals 12-1 and 12-2, responsive to incident light. The optical detector circuits 120-1 and 120-2 may be part of optical detector 120 from FIG. 1, where each of the individual optical detector circuits 120-1 and 120-2 may correspond to one photodetector circuit in an array.

The optical detector circuits 120-1 and 120-2 may optionally each include an amplifier 210-1 and 210-2. The amplifiers may be voltage amplifiers or current amplifiers (e.g., transimpedance amplifiers), depending on the specific implementation. The output of the photodetector devices in the optical detector circuits 120-1 and 120-2 may thus correspond to an electrical signal (21-1, 21-2) that is coupled to a respective input to one of the amplifiers 210-1 and 210-2. Thus, the electrical 21-1 of optical detector circuit 120-1 is coupled to an input of amplifier 210-1; and electrical signal 21-2 of optical detector circuit 120-2 is coupled to an input of amplifier 210-2.

Each of the amplifiers 120-1 and 120-2 may receive an electrical signal from a respective photodetector in the optical detector circuits 120-1 and 120-2; and generate an analog detection signal 12-1 and 12-2, which is proportional to the corresponding electrical signal. Thus, analog detection signal 12-1 is proportional to electrical signal 21-1 and analog detection signal 12-2 is proportional to electrical signal 21-2. In some examples, the electrical signals correspond to a current that is output from a photodetector, and the analog detection signals correspond to a voltage, where a transimpedance amplifier converts the photodetector current into an analog voltage.

Analog detection signal 12-1 is coupled to an input of the first saturation detector 230-1, a first input (path 0) of a first path selector 240-1, and a second input (path 1) of a second path selector 240-2. Analog detection signal 12-2 is coupled to an input of the second saturation detector 230-2, a second input (path 1) of the first path selector 240-1, and a first input (path 0) of the second path selector 240-2.

The first saturation detector 230-1 is configured to generate a first selector signal 23-1, which has a logic value of logic 1 or 0 based on a signal level associated with the analog detection signal 12-1. When analog detection signal 12-1 has an amplitude (or value) that is below a threshold (e.g., VREF1), then saturation detector 230-1 will set the first selector signal 23-1 to a first value (e.g., 0). Similarly, when analog detection signal 12-1 has an amplitude (or value) that is above a threshold (e.g., VREF1), then saturation detector 230-1 will set the first selector signal 23-1 to a second value (e.g., 1). The first path selector 240-1 will select a path for either signal 12-1 or signal 12-2 based on the value of the first selector signal 23-1. When the first selector signal 23-1 is the first value, path selector 240-1 couples analog detection signal 12-1 to a first input of the summer 250 as signal 24-1; otherwise path selector 240-1 couples analog detection signal 12-2 to the first input of the summer 250 as signal 24-1.

The second saturation detector 230-1 is configured to generate a second selector signal 23-2, which has a logic value of logic 1 or 0 based on a signal level associated with the analog detection signal 12-2. When analog detection signal 12-2 has an amplitude (or value) that is below a threshold (e.g., VREF2), then saturation detector 230-2 will set the second selector signal 23-2 to a first value (e.g., 0). Similarly, when analog detection signal 12-2 has an amplitude (or value) that is above a threshold (e.g., VREF2), then saturation detector 230-2 will set the second selector signal 23-2 to a second value (e.g., 1). The second path selector 240-2 will select a path for either signal 12-1 or 12-2 based on the value of the second selector signal 23-2. When the second selector signal 23-2 is the first value, path selector 240-2 couples analog detection signal 12-2 to a second input of the summer 250 as signal 24-2; otherwise path selector 240-2 couples analog detection signal 12-1 to the second input of the summer 250 as signal 24-2.

The signals 23-1 and 23-2 also correspond to signals S1 and S2, respectively, and may be output to the processor (e.g., processor 170 of FIG. 1) to assist in forming a map or image that may be used for eye-tracking or other uses; similar to signal 32 of FIG. 1.

Summer 250 is an analog signal summer that is configured to combine the signals 24-1 and 24-2 into a combined analog signal 25, which is input to the ADC 260. The ADC converts the combined analog signal 25 into a digital signal 26, which may be further processed by a processor (e.g., processor 170 of FIG. 1). Considering signal 12-1 as A1, signal 12-2 as A2, signal 24-1 as B1, signal 24-2 as B2, and signal 25 as C, the following chart is helpful in understanding the signal paths:

TABLE 1

| Level of A1 | Level of A2 | B1 | B2 | C | Comment |
|---|---|---|---|---|---|
| A1 < VREF1 | A2 < VREF2 | A1 | A2 | A1 + A2 | No Specular Reflection Detected |
| A1 > VREF1 | A2 < VREF2 | A2 | A1 | A2 + A2 | Specular Reflection Detected on A1 |
| A1 < VREF1 | A2 > VREF2 | A1 | A1 | A1 + A1 | Specular Reflection Detected on A2 |

TABLE 1-continued

| Level of A1 | Level of A2 | B1 | B2 | C | Comment |
|---|---|---|---|---|---|
| A1 > VREF1 | A2 > VREF2 | A2 | A1 | A1 + A2 | Specular Reflection on both A1 and A2 (theoretically, this case should not occur) |

Figure 3:
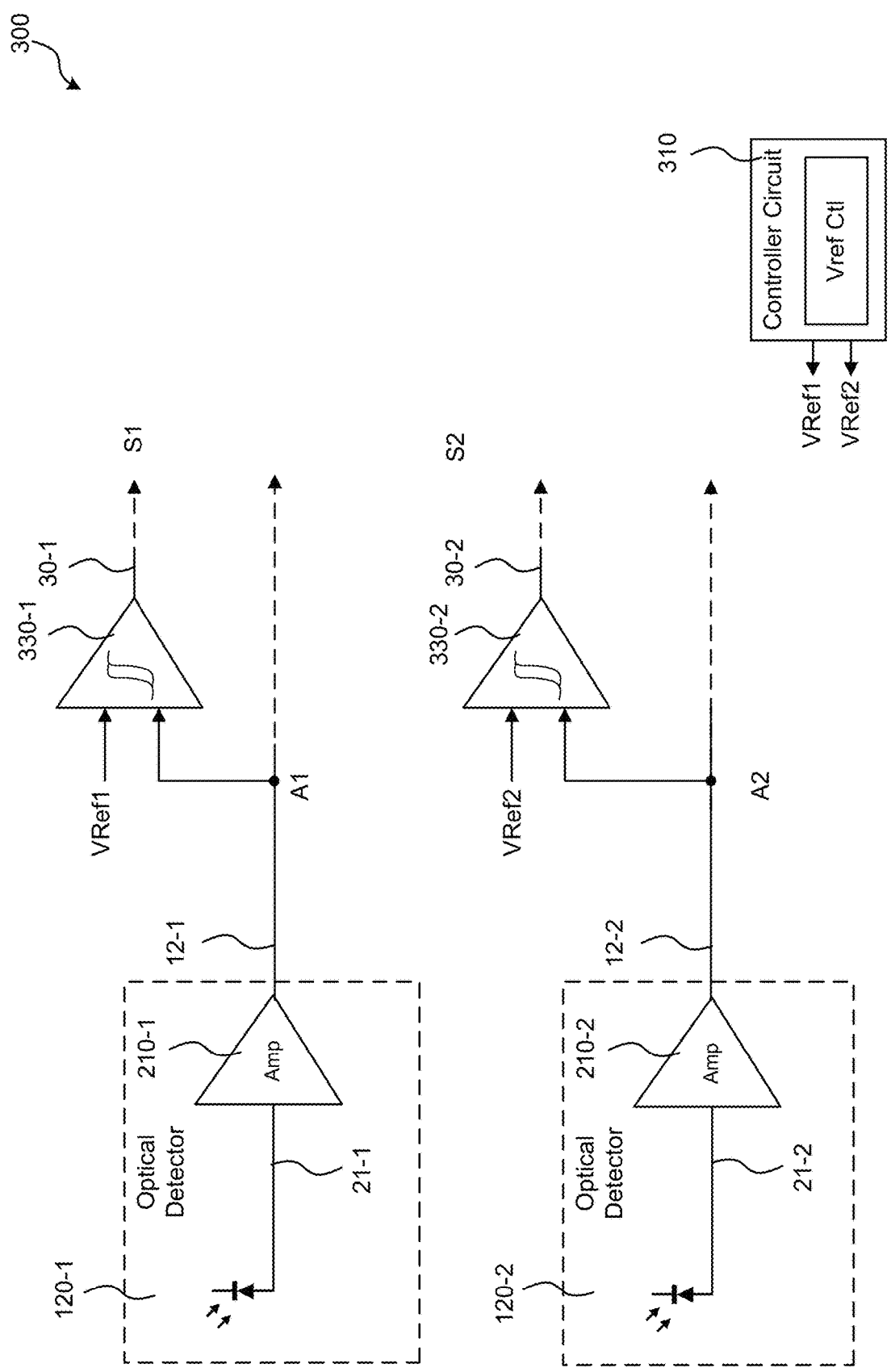
FIG. 3 shows a partial view of yet another example imager system.

FIG. 3 shows a partial view of yet another example imager system 300, arranged in accordance with at least some aspects described herein. System 300 is substantially similar to system 200 of FIG. 2, with the addition of example saturation detector circuits 330-1 and 330-2, and controller circuit 310.

Saturation detector circuit 330-1 includes a first input coupled to analog detection signal 12-1 or A1, a second input coupled to VREF1, and an output coupled to 30-1 or S1. Saturation detector circuit 330-2 includes a first input coupled to analog detection signal 12-2 or A2, a second input coupled to VREF2, and an output coupled to 30-2 or S2. Saturation detector circuits 330-1 and 330-2 replace saturation detectors 230-1 and 230-2 from FIG. 2, and thus the outputs 30-1 and 30-2 substantially correspond to 23-1 and 23-2 from FIG. 2.

The example saturation detector circuits 330-1 and 330-2 of FIG. 3 are shown as comparator circuits. For example, saturation detector circuit 330-1 is configured to compare analog detection signal 12-1 or A1 to VREF1 and assert selector signal 30-1 or S1 in response to the comparison. Similarly, saturation detector circuit 330-2 is configured to compare analog detection signal 12-2 or A2 to VREF2 and assert selector signal 30-2 or S2 in response to the comparison. The signals 30-1 and 30-2 (S1 and S2), may be output to the processor (e.g., processor 170 of FIG. 1); similar to signal 32 of FIG. 1.

Controller circuit 310 is configured to adjust the values of the thresholds for each of the comparators, by adjusting VREF1 and VREF2. In a simple example, VREF1=VREF2. In other examples, VREF1 and VREF2 are independently set. The independent adjustment of VREF1 and VREF2 may be preferred in examples where the optical detector circuits (including any photodetectors, amplifiers, etc.) and/or comparators are not exactly matched in performance, allowing a calibration of the thresholds.

The saturation detection circuits 330-1 and 330-2 may employ hysteresis to offer some level of immunity from instability that may occur when a comparator is on the edge of tripping. For example, when A1 is very close to VREF1 and there is a noise signal present in either input signal, there is a possibility that the saturation detection circuit 330-1 will thrash back and forth, and inject noise into the B1 signal. By adding hysteresis to the input of the comparators, the exact signal thresholds for a 0→1 change will be different that that for a 1→0 change, which will prevent the comparator oscillating or thrashing back and forth.

Figure 4:
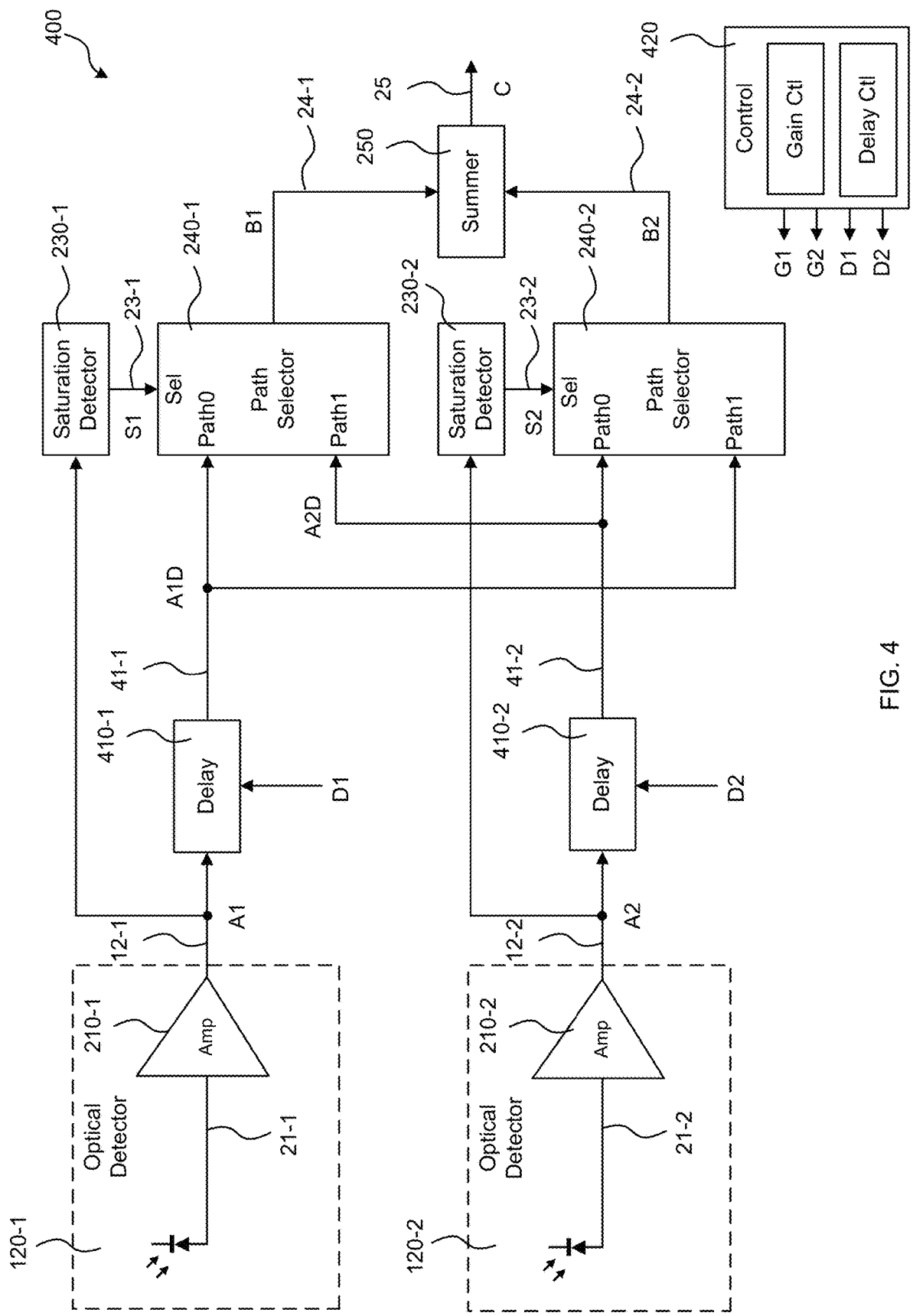
FIG. 4 shows a partial view of still another example imager system.

FIG. 4 shows a schematic diagram of another example imager system 400 that is arranged in accordance with the presently disclosed techniques. System 400 includes optical detector circuits 120-1 and 120-2 saturation detectors 230-1 and 230-2, path selectors 240-1 and 240-2, and summer 250; all substantially similar to system 200 of FIG. 2. System 400 further includes example delay circuits 410-1 and 410-2, and an example controller 420.

Delay circuit 410-1 of FIG. 4 is inserted between the first optical detector circuit 120-1 and the first path selector 240-1 of FIG. 2. Thus, analog detection signal 12-1 or A1 is coupled to an input of delay circuit 410-1, and an output signal 41-1 or A1D of delay circuit 410-1 is coupled to a first input (Path 0) of the first path selector 240-1, and a second input (Path 1) of the second path selector 240-2.

Delay circuit 410-2 of FIG. 4 is inserted between the second optical detector circuit 120-2 and the second path selector 240-2 of FIG. 2. Thus, analog detection signal 12-2 or A2 is coupled to an input of delay circuit 410-2, and an output signal 41-2 or A2D of delay circuit 410-2 is coupled to a second input (Path 1) of the first path selector 240-1, and the first input (Path 0) of the second path selector 240-2.

Operationally, delay circuits 410-1 and 410-2 are configured to delay the input signals to the path selectors from changing prior to the evaluation of the signals by the saturation detectors. This guarantees that the saturation detectors will select a path prior to the path selectors coupling their selected paths to the inputs of the summer 250. For example, if a specular reflection is detected by saturation detector 230-2 by analog detection signal 12-2 or A2 exceeding a threshold signal (e.g., A2>VREF2), the path selector 240-2 will change from Path0 to Path1 prior to a the analog detection signal 12-2 or A2 reaching the output signal 41-2 of the delay 410-2, and thus preventing a signal transition from being coupled to the input of Summer B2.

The delay circuits 310-1 and 410-2 may optionally be adjusted for an amount of delay in response to one or more control signals D1 or D2 from the controller circuit 420. The adjustment of delay time may be desirable to guarantee proper performance without any excessive delays. Additionally, delay time may in one direction (e.g., from a 0→1 transition) may be different from a delay time in the other direction (e.g., from a 1→0 transition).

Amplifiers may be included in the optical detector circuits 120-1 and 120-2 as illustrated by amplifiers 210-1 and 210-2. These amplifiers may optionally be adjusted for an amount of gain in response to one or more control signals G1 or G2 from the controller circuit 420. The adjustment in gain may be desirable to guarantee proper performance by calibrating the signal gain for each of the optical detector circuits 120-1 and 120-2.

Figure 5:
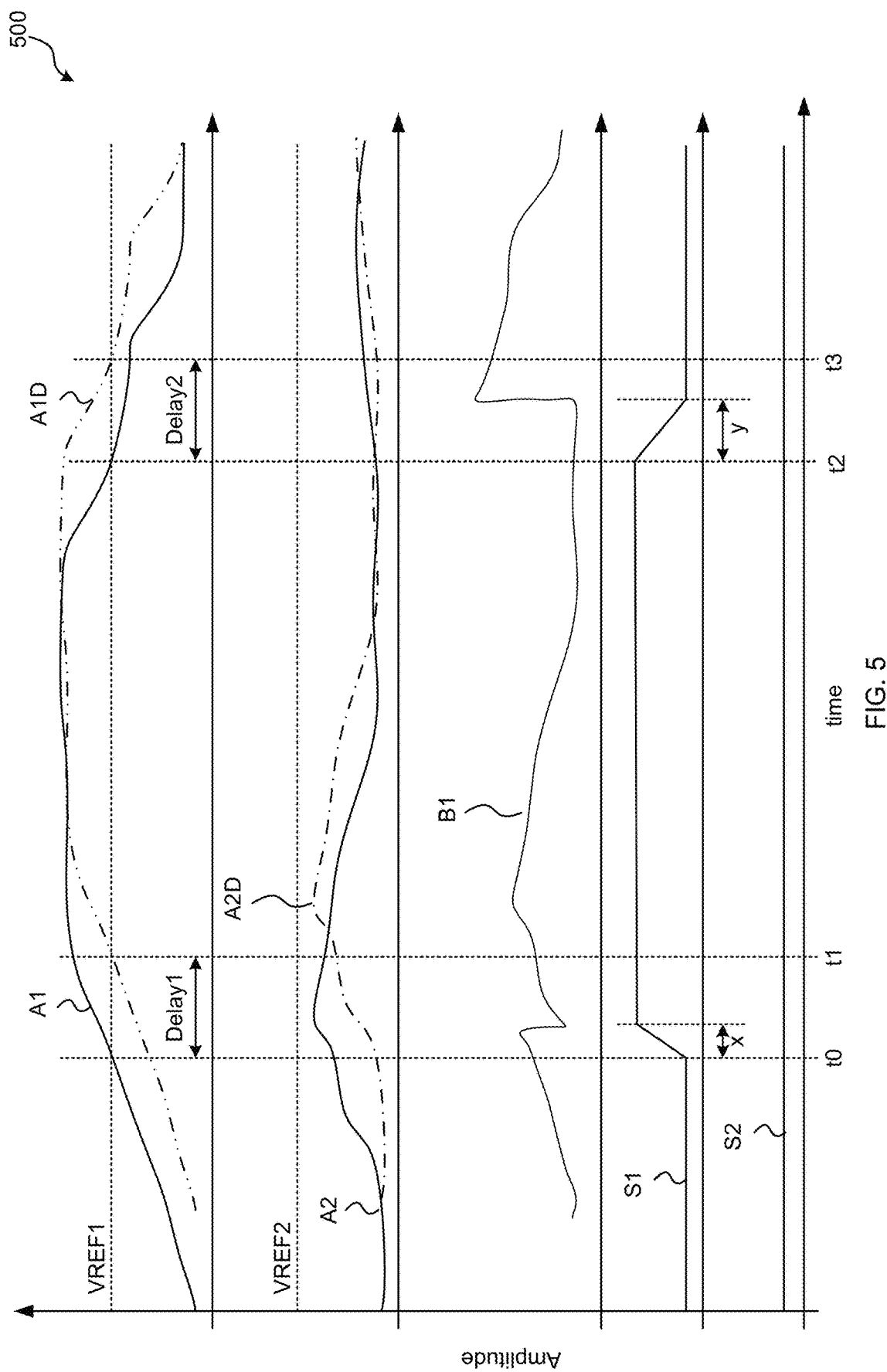
FIG. 5 shows a graph of example signals in an example imager system.

FIG. 5 shows a graph of example signals 500 in an example eye tracking imager system such as system 400 of FIG. 4. The example graph shows signal A1, A1D, A2, A2D, B1, S1 and S2.

As illustrated, selection signals S1 and S2, from the saturation detectors, are initially low in value, and signal B1 initially corresponds to signal A1, which is the output 12-1 of optical detector circuit 120-1. At time t0, signal A1 exceeds a threshold voltage (A1>VREF1), which indicates that signal A1 has saturated as a result of a specular reflection. However, at this time signal A2 is below the threshold for saturation detection (A2<VREF2), which indicates that signal A2 has not saturated.

After a small delay time (x) from time t0, selector signal S1 transitions from a low signal (Logic 0) to high signal (Logic 1), and first path selector 240-1 changes the path selected from path0 to path1. Once path1 is selected, the output 12-2 or A2 of optical detector circuit 120-2, is coupled through path selector 240-1 to signal B1 at the input to Summer 150. However, signal A1 and A2 are delayed by a first amount (i.e., Delay1>x, and t1=t0+Delay1) by the delay circuit 410-1 and 410-2, and thus the switch path path0 to path1 is completed before time t1, and thus the input B1 to summer 150 has not reached saturation and signal integrity is preserved.

At time t2, the signal A1 dips below the threshold voltage VREF1 for saturation detection, and after another delay (y) the selector signal 51 transitions from a high signal (Logic 1) back to a low signal (Logic 0). In this example, the delay after the threshold crossing (A1<VREF1) crossing is again longer than the delay for switching the path from path1 back to path0 (i.e., Delay2>y, and t3=t2+Delay2).

The various signals illustrated in FIG. 5 are for illustration purposes, actual signals may have a different shape based on the response time and intensity of incident light upon the photodetector circuit.

Figure 6:
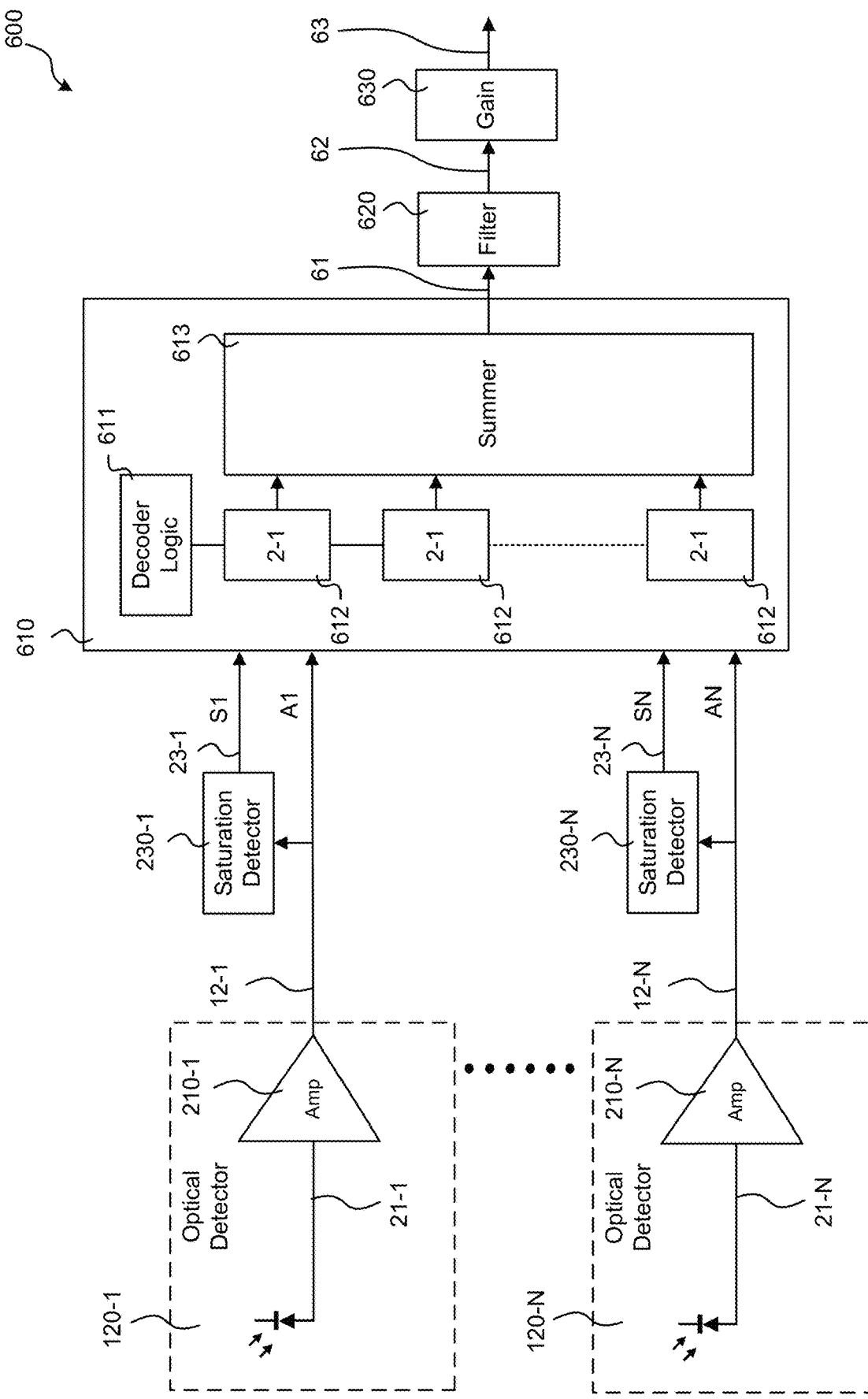
FIG. 6 shows a partial view of still yet another example imager system.

FIG. 6 shows a partial view of still yet another example imager system 600, arranged in accordance with the presently disclosed techniques. System 600 include an optical detector circuit 120-1 and a saturation detector 230-1; all substantially similar to systems described for FIGS. 1-4. However, system 600 illustrates an array implementation with N optical detector circuits 210-1: N (each shown with an optional amplifier 210-1:N) and N saturation detectors 230-1:N; yielding analog detection signals 12-1: N, and N selection signals S1:N.

FIG. 6 also includes a signal combiner 610, which includes a decoder logic 611, an array of 2-1 multiplexers 612, and a summer 613. Each of the 2-1 multiplexers 612 is configured to receive a pair of inputs from two different optical detector circuits, such as illustrated in FIG. 2. The outputs of all of the multiplexers are combined by the summer 613.

A first input of each of the multiplexers 612 is coupled to an output of a respective one of the optical detector circuits 120-1: N. For example, an output of the first optical detector circuit 120-1 is coupled to a first input of a first one of the multiplexers 612, an output of the second optical detector circuit 120-2 is coupled to a first input of a second one of the multiplexers 612, and an output of an Nth optical detector circuit 120-N is coupled to a first input to an Nth one of the multiplexers 612. A second input to each of the multiplexers 612 is coupled to one of the other optical detector circuits. For example, the second input of the first multiplexer may corresponds to an output of one of optical detector circuits 120-2:N; while the second input of the second multiplexer may correspond to an output of one of optical detector circuits 120-1, 120-3:N. The choice of the first and second inputs to the multiplexers may preferably be optical detector circuits that are reasonably in close proximity since the signal levels between adjacent optical detectors may be closer in overall amplitude.

Given that it is highly unlikely that more than one specular reflection will occur for a scan, the adjacent pairs should be able to provide an improved signal level since the specular reflection will be rejected by the saturation detectors. The decoder logic receives the various inputs from the saturation detectors S1:N and generates control signals for each of the multiplexers 612. Thus, the paths from each of the multiplexers will be selected based on those signals that are preferably below the saturation threshold of the corresponding saturation detector, promoting the non-saturated signals from the optical detector circuits (120-1:N) for summation by the summer 613.

The output of the summer 613 can again be coupled to an ADC circuit, or optionally to a filter 620 and/or a gain stage 630. As described earlier, gain and/or filtering of the output signal from the summer can be utilized to improve the signal to noise ratio of the signal for the ADC.

Figure 7:
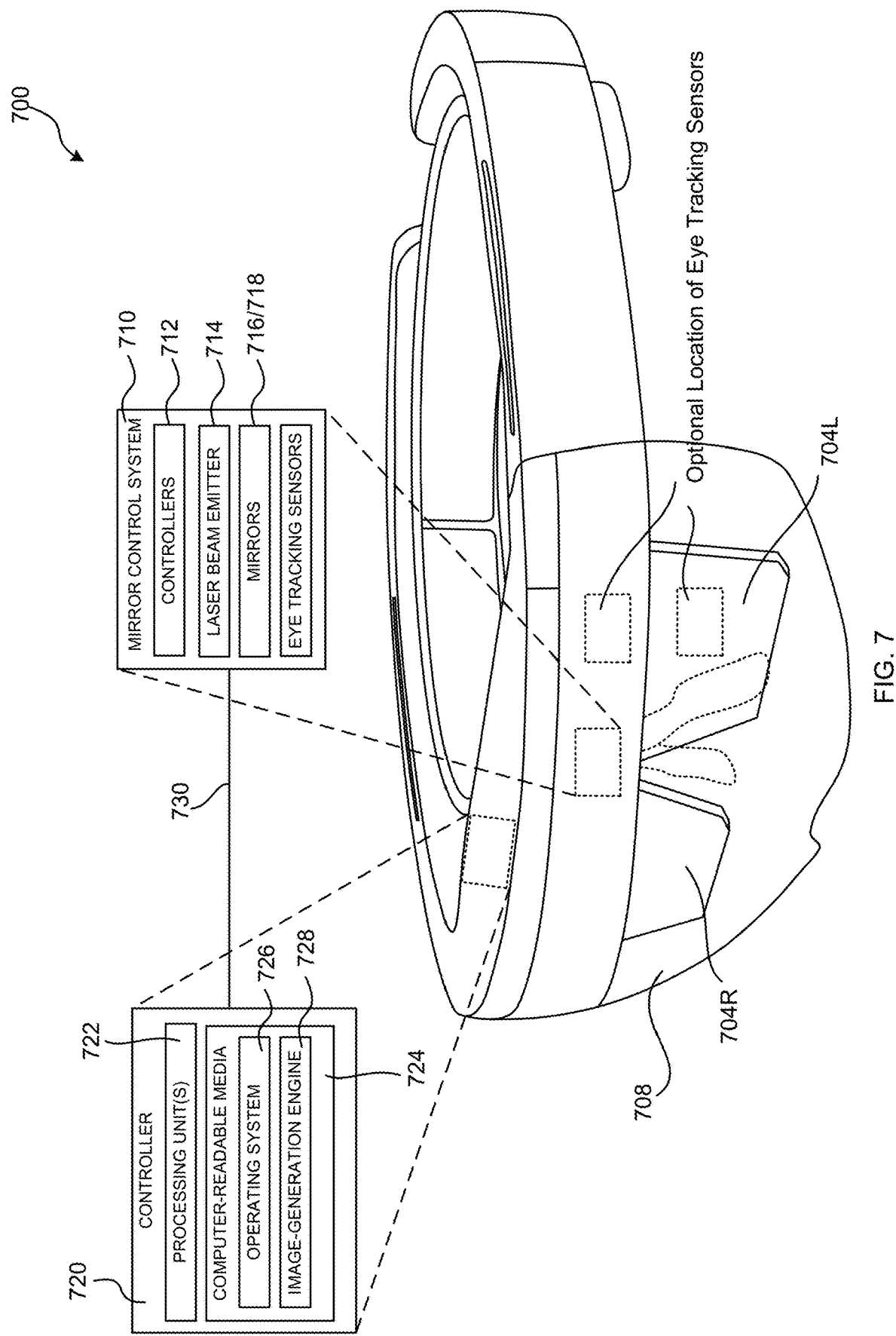
FIG. 7 shows the display device in the form of a head-mounted display device.

FIG. 7 shows the display device in the form of a head-mounted display device. The head-mounted display may be a near-eye display ("NED") device 700 that includes a mirror control system 710 implementing aspects of the technologies disclosed herein. The mirror control system 710 includes the laser beam emitter 714, mirrors 716 and 718, and controllers 712.

In some examples, the NED device 700 may utilize the mirror control system 710 to generate a composite view (e.g., from a perspective of a user that is wearing the NED device 700) that includes both one or more computer-generated ("CG") images and a view of at least a portion of a real-world environment surrounding the NED device 700. For example, the mirror control system 710 may utilize various technologies such as, for example, augmented reality ("AR") technologies to generate composite views that include CG images superimposed over a real-world view. As such, the mirror control system 710 may be configured to generate CG images via a display panel 704.

In the illustrated example, the display panel 704 includes separate right eye and left eye transparent display panels, labeled 704R and 704L, respectively. In some examples, the display panel 704 may include a single transparent display panel that is viewable with both eyes and/or a single transparent display panel that is viewable by a single eye only.

It can be appreciated that the techniques described herein may be deployed within a single-eye NED device 700 (e.g. GOOGLE GLASS) and/or a dual-eye NED device 700 (e.g. MICROSOFT HOLOLENS). The NED device 700 shown in FIG. 7 is an example device that is used to provide context and illustrate various features and aspects of the mirror control system 710 disclosed herein. Other devices and systems may also use the mirror control system 710 disclosed herein.

In some examples, the display panel 704 may be a waveguide display that includes one or more diffractive optical elements ("DOEs") for in-coupling incident light into a waveguide, expanding the incident light in one or more directions for exit pupil expansion, and/or out-coupling the incident light out of the waveguide (e.g., toward a user's eye). In some examples, the NED device 700 may further include an additional see-through optical component in the form of a transparent veil 708 positioned between the real-world environment (which real-world environment makes up no part of the claimed invention) and the display panel 704.

It can be appreciated that the transparent veil 708 may be included in the NED device 700 for purely aesthetic and/or protective purposes. The NED device 700 may further include various other components, for example speakers, microphones, accelerometers, gyroscopes, magnetometers, temperature sensors, touch sensors, inertial measurement sensors, biometric sensors, other image sensors, energy-storage components (e.g. battery), a communication facility, a global positioning system ("GPS") receiver, etc.

In the illustrated example, a controller 720 is operatively coupled to the mirror control system 710. The controller 720 includes one or more logic devices and one or more computer memory devices storing instructions executable by the logic device(s) to deploy aspects of the functionality described herein with relation to the mirror control system 710. The controller 720 and the mirror control system 710 of the NED device 700 are operatively connected, for example, via a bus 730, which can include one or more of a system bus, a data bus, an address bus, a PCI bus, a Mini-PCI bus, and any variety of local, peripheral, and/or independent buses.

The controller 720 can also include one or more processing units 722. The processing unit(s) 722, can represent, for example, a CPU-type processing unit, a GPU-type processing unit, a field-programmable gate array ("FPGA"), a digital signal processor ("DSP"), or other hardware logic components that may, in some instances, be driven by a CPU. For example, and without limitation, illustrative types of hardware logic components that can be used include Application-Specific Integrated Circuits ("ASICs"), Application-Specific Standard Products ("ASSPs"), System-on-a-Chip Systems ("SOCs"), Complex Programmable Logic Devices ("CPLDs"), etc.

The controller 720 can also include one or more computer-readable media 724 storing an operating system 726 and data such as, for example, image data that defines one or more CG images for presentation by the NED device 700. The computer-readable media 724 may further include an image-generation engine 728 that generates output signals to control aspects of the operation of the mirror control system 710 to present the CG images.

As used herein, computer-readable media, such as computer-readable media 724, can store instructions executable by the processing units 722. The computer-readable media 724 can also store instructions executable by external processing units such as by an external CPU, an external GPU, and/or executable by an external accelerator, such as an FPGA type accelerator, a DSP type accelerator, or any other internal or external accelerator. In various examples, at least one CPU, GPU, and/or accelerator is incorporated in the NED device 700, while in some examples one or more of a CPU, GPU, and/or accelerator are external to the NED device 700.

As used herein, the term computer-readable media can include computer storage media and/or communication media. Computer storage media can include one or more of volatile memory, nonvolatile memory, and/or other persistent and/or auxiliary computer storage media, removable and non-removable computer storage media implemented in any method or technology for storage of information such as computer-readable instructions, data structures, program modules, or other data.

Thus, computer storage media includes tangible and/or physical forms of media included in a device and/or hardware component that is part of a device or external to a device, including but not limited to random access memory ("RAM"), static random-access memory ("SRAM"), dynamic random-access memory ("DRAM"), phase change memory ("PCM"), read-only memory ("ROM"), erasable programmable read-only memory ("EPROM"), electrically erasable programmable read-only memory ("EEPROM"), flash memory, rotating media, optical cards or other optical storage media, magnetic storage, magnetic cards or other magnetic storage devices or media, solid-state memory devices, storage arrays, network attached storage, storage area networks, hosted computer storage or any other storage memory, storage device, and/or storage medium that can be used to store and maintain information for access by a computing device in a non-transitory fashion.

In contrast to computer storage media, communication media can embody computer-readable instructions, data structures, program modules, or other data in a modulated data signal, such as a carrier wave, or other transmission mechanism. As defined herein, computer storage media does not include communication media. That is, computer storage media does not include communications media consisting solely of a modulated data signal, a carrier wave, or a propagated signal, per se.

Figure 8:
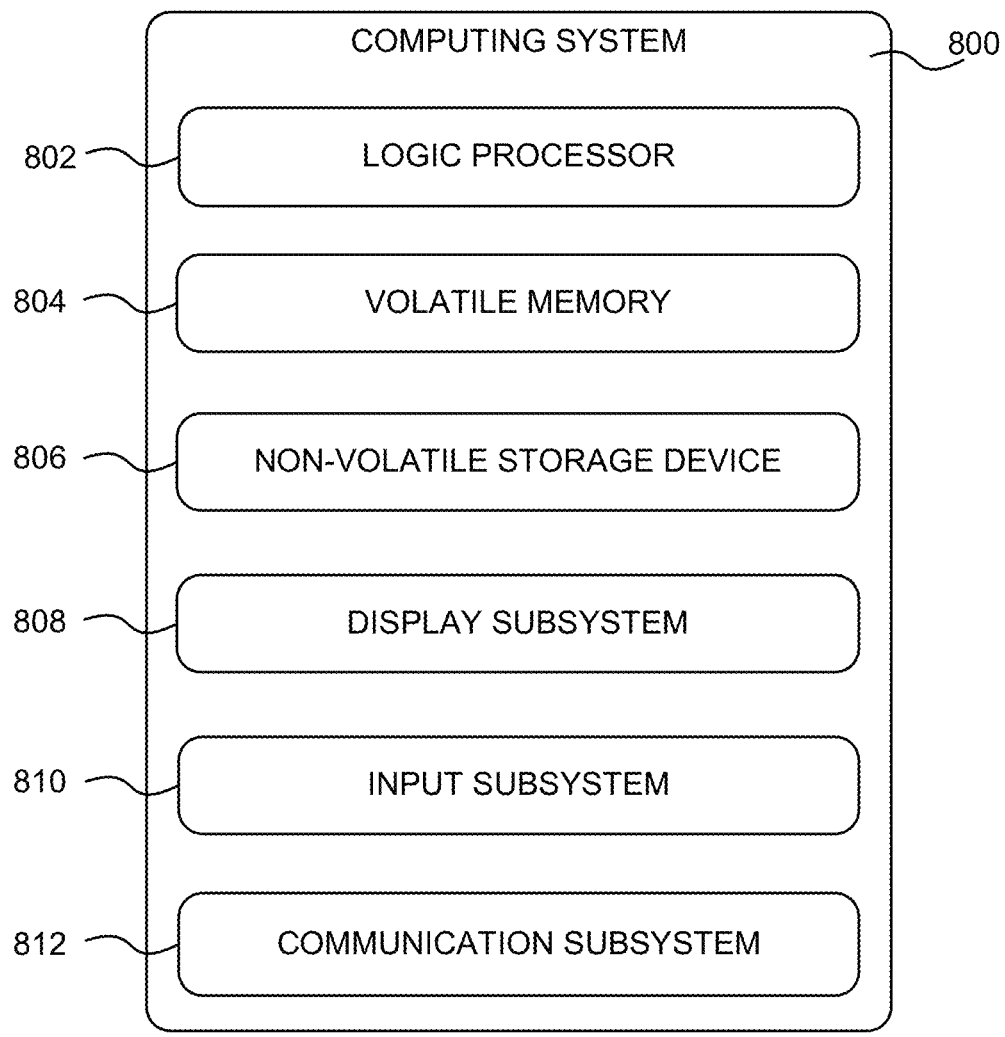
FIG. 8 shows an example computing environment in which the computer device may be enacted.

FIG. 8 shows an example computing environment in which aspects of the technologies disclosed herein can be implemented. In particular, FIG. 8 schematically shows a non-limiting embodiment of a computing system 800 that can be used to implement the technologies disclosed herein. Computing system 800 may take the form of one or more personal computers, server computers, tablet computers, home-entertainment computers, network computing devices, gaming devices, mobile computing devices, mobile communication devices (e.g., smart phone), and/or other computing devices, and wearable computing devices such as smart wristwatches and head mounted augmented reality devices.

Computing system 800 includes a logic processor 802 volatile memory 804, and a non-volatile storage device 806. Computing system 800 may optionally include a display subsystem 808, input subsystem 810, communication subsystem 812, and/or other components not shown in FIG. 8.

Logic processor 802 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor 802 may include one or more physical processors (e.g. hardware) configured to execute software instructions. Additionally, or alternatively, the logic processor 802 may include one or more hardware logic circuits or firmware devices configured to execute hardware-implemented logic or firmware instructions.

The logic processor 802 may be single-core or multi-core, and the instructions executed thereon may be configured for sequential, parallel, and/or distributed processing. Individual components of the logic processor 802 optionally may be distributed among two or more separate devices, which may be remotely located and/or configured for coordinated processing. Aspects of the operation of the logic processor 802 may be virtualized and executed by remotely accessible, networked computing devices configured in a cloud-computing configuration. In such a case, these virtualized aspects are run on different physical logic processors of various different machines, it will be understood.

Non-volatile storage device 806 includes one or more physical devices configured to hold instructions executable by the logic processors to implement aspects of the methods and processes described herein. When such methods and processes are implemented, the state of non-volatile storage device 806 may be transformed—e.g., to hold different data.

Non-volatile storage device 806 may include physical devices that are removable and/or built in. Non-volatile storage device 806 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 806 may include nonvolatile, dynamic, static, read/write, read-only, sequential-access, location-addressable, file-addressable, and/or content-addressable devices. It will be appreciated that non-volatile storage device 806 is configured to hold instructions even when power is cut to the non-volatile storage device 806.

Volatile memory 804 may include physical devices that include random access memory. Volatile memory 804 is typically utilized by logic processor 802 to temporarily store information during processing of software instructions. It will be appreciated that volatile memory 804 typically does not continue to store instructions when power is removed from the volatile memory 804. Aspects of logic processor 802, volatile memory 804, and non-volatile storage device 806 may be integrated together into one or more hardware-logic components, such as within an ASIC, SOC, or FPGA.

The terms "module," "program," and "engine" may be used to describe an aspect of computing system 800 typically implemented in software by a processor 802 to perform a particular function using portions of volatile memory 804, which function involves transformative processing that specially configures the processor 802 to perform the function. Thus, a module, program, or engine may be instantiated via logic processor 802 executing instructions held by non-volatile storage device 806, using portions of volatile memory 804.

It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 808 may be used to present a visual representation of data held by non-volatile storage device 806. The visual representation may take the form of a graphical user interface ("GUI"). As the herein described methods and processes change the data held by the non-volatile storage device, and thus transform the state of the non-volatile storage device, the state of display subsystem 808 may likewise be transformed to visually represent changes in the underlying data. Display subsystem 808 may include one or more display devices utilizing virtually any type of technology, such as the LBS display devices disclosed herein. Such display devices may be combined with logic processor 802, volatile memory 804, and/or non-volatile storage device 806 in a shared enclosure, or such display devices may be peripheral display devices.

When included, input subsystem 810 may comprise or interface with one or more user-input devices such as a keyboard, mouse, touch screen, or game controller. In some embodiments, the input subsystem may comprise or interface with selected natural user input ("NUI") componentry. Such componentry may be integrated or peripheral, and the transduction and/or processing of input actions may be handled on- or off-board.

Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 812 may be configured to communicatively couple various computing devices described herein with each other, and with other devices. Communication subsystem 812 may include wired and/or wireless communication devices compatible with one or more different communication protocols. As non-limiting examples, the communication subsystem may be configured for communication via a wireless telephone network, or a wired or wireless local- or wide-area network, such as a HDMI over Wi-Fi connection. In some embodiments, the communication subsystem may allow computing system 800 to send and/or receive messages to and/or from other devices via a network such as the Internet.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The disclosure presented herein also encompasses the subject matter set forth in the following clauses:

Clause 1: A device to detect and process light reflected from an eye of a user, the device comprising: a first optical detector circuit (120-1) that provides a first analog detection signal (12-1) responsive to a first incident light reflected from the eye of the user; a second optical detector circuit (120-2) that provides a second analog detection signal (12-2) responsive to a second incident light reflected from the eye of the user; a first path selector (240-1) with a first input to receive the first analog detection signal (12-1), a second input to receive the second analog detection signal (12-2), a control input to receive a first selection signal (23-1), and an output (24-1) to selectively couple one of the first and second inputs to the output responsive to the first selection signal (23-1); a second path selector (240-2) with a first input to receive the second analog detection signal (12-2), a second input to receive the first analog signal (12-1), a control input to receive a second selection signal (23-2), and an output (24-2) to selectively couple one of the first and second inputs to the output responsive to the second selection signal; and a summer (250) with a first input that is coupled to the output of the first path selector (24-1), a second input that is coupled to the output of the second path selector (24-2), and generate a combined analog signal (25) as a summation of the first and second inputs to the summer.

Clause 2: The device of any of the example clauses, further comprising: an analog-to-digital converter to receive the combined analog signal, sample the combined analog signals, and generate a digital signal as a conversion of the sampled analog signal into a digital value.

Clause 3: The device of any of the example clauses, further comprising a processor that is configured to receive the digital signals from the analog-to-digital converter, generate a first image of the eye of the user based on the digital signal at a first time, generate a second image of the eye of the user based on the digital signal at a second time, and determine a direction of gaze or movement of the eye based on a comparison of the first image and the second image.

Clause 4: The device of any of the example clauses, further comprising: a first saturation detector to receive the first analog detection signal and generate the first selection signal responsive to a comparison of the first analog detection signal to a first threshold; and a second saturation detector to receive the second analog detection signal and generate the second selection signal responsive to a comparison of the second analog detection signal to a second threshold.

Clause 5: The device of any of the example clauses, wherein the first and second thresholds are the same.

Clause 6: The device of any of the example clauses, wherein the first and second saturation detectors each correspond to a comparator with hysteresis.

Clause 7: The device of any of the example clauses, further comprising: a first delay circuit that is coupled between the first optical detector circuit and the first and second path selectors, wherein the first delay circuit generates a first delayed analog signal that is delayed in time with respect to the first analog detection signal; and a second delay circuit that is coupled between the second optical detector circuit and the first and second path selectors, wherein the second delay circuit generates a second delayed analog signal that is delayed in time with respect to the second analog detection signal.

Clause 8: The device of any of the example clauses, further comprising: a third optical detector circuit that provides a third analog detection signal responsive to a third incident light reflected from the eye of the user; a third path selector with a first input to receive the third analog detection signal, a second input to receive one of the first or second analog detection signals, a control input to receive a third selection signal, and an output to selectively couple one of the first and second inputs to the output responsive to the third selection signal; and wherein the summer is further includes a third input that is coupled to the output of the third path selector, wherein the summer generates the combined analog signal as a summation of the first, second, and third inputs to the summer.

Clause 9: The device of any of the example clauses, further comprising: a first saturation detector to receive the first analog detection signal and generate the first selection signal responsive to a comparison of the first analog detection signal to a first threshold; a second saturation detector to receive the second analog detection signal and generate the second selection signal responsive to a comparison of the second analog detection signal to a second threshold; and a third saturation detector to receive the third analog detection signal and generate the third selection signal responsive to a comparison of the third analog detection signal to a third threshold.

Clause 10: The device of any of the example clauses, further comprising: an optical filter that is located between each optical detector circuit and the light incident on the optical detector circuit, wherein the optical filter comprises one or more of: a first filter that selectively blocks wavelengths that are different from an incident beam, a second filter that selectively blocks undesired ambient light, a third filter that selectively blocks light in the red, green, or blue light spectrums, a fourth filter that blocks light in the visible spectrum, a fifth filter that selectively blocks light a wavelength in a specific portion of the infrared wavelength spectrum, or a sixth filter that passes light with a specific polarization.

Clause 11: The device of any of the example clauses, further comprising: an analog filter that filters the combined analog signal prior to generate a filtered signal, wherein the analog filter comprises one or more of a passive filter, an active filter, a low-pass filter, a high-pass filter, a band-pass filter, or a phase-shape filter; and an analog-to-digital converter that receives the filtered signal and converts the filtered signal to a digital value.

Clause 12: The device to detect and process incident light reflected from an eye of a user, the device comprising: an array of optical detectors (120-1, N), each configured to provide a corresponding one of an array of analog detection signals (12-1, N) responsive to a corresponding incident light reflected from the eye of the user; an array of saturation detectors (230-1, N), each configured to receive the corresponding array of analog detection signal (12-1, N) and generate a corresponding selection signal (23-1, N) responsive to a comparison of the corresponding analog detection signal (23-1, N) to a corresponding threshold; and a signal combiner (130, 610) configured to receive the plurality of selection signals (23-1, N) and the plurality of analog detection signals (12-1, N), wherein the signal combiner (610) is configured to selectively combine the plurality of analog detection signals (12-1, N) to generate a combined analog signal (31, 61) based on the array of selection signals (23-1, N), wherein non-saturated signals are promoted over saturated signals in the combined analog signal (31, 61).

Clause 13: The device of any of the example clauses, wherein the signal combiner comprises: a decoder logic that generates control signals based on the selection signals from the saturation detectors; a set of multiplexers, where each of the multiplexers receives two different ones of the analog detection signals; and a summer, wherein the summer is configured to combine the outputs of the set of multiplexers to generate the combined analog signal.

Clause 14: The device of any of the example clauses, further comprising: an analog-to-digital converter to receive the combined analog signal, sample the combined analog signals, and generate a digital signal as a conversion of the sampled analog signal into a digital value; and a processor that is configured to receive the digital signals from the analog-to-digital converter, generate a first image of the eye of the user based on the digital signal at a first time, generate a second image of the eye of the user based on the digital signal at a second time, and determine a direction of gaze or movement of the eye based on a comparison of the first image and the second image.

Clause 15: A device to generate an electrical response to light incident (10-1, N) that light includes specular and scattered reflections from the eye of a user, the device comprising: an optical detector (120) that generates a plurality of electrical signals (12-1, N) responsive to the light incident on the optical detector (120); a signal combiner (130) that receives the plurality of electrical signals (12-1, N) from the optical detector (120), evaluates a signal level of each of the plurality of electrical signals (12-1, N) to determine when the signal level of the corresponding one of the plurality of electrical signals has saturated, and selectively combines the plurality of electrical signals (12-1, N) to generate a combined analog signal (31) based on the determined signal levels such that non-saturated signals are promoted over saturated signals in the combined analog signal (31); and an analog-to-digital converter (150) that receives the combined analog signal (31) from the signal combiner (130), samples the combined analog signals, and generates a digital signal (51) as a conversion of the sampled analog signal into a digital value.

Clause 16: The device of any of the example clauses, further comprising: an optical filter that is located between the optical detector and the light incident on the optical detector, wherein the optical filter comprises one or more of: a first filter that selectively blocks wavelengths that are different from an incident beam, a second filter that selectively blocks undesired ambient light, a third filter that selectively blocks light in the red, green, or blue light spectrums, a fourth filter that blocks light in the visible spectrum, a fifth filter that selectively blocks light a wavelength in a specific portion of the infrared wavelength spectrum, or a sixth filter that passes light with a specific polarization.

Clause 17: The device of any of the example clauses, further comprising: an analog filter that filters the combined analog signal prior to sampling by the analog-to-digital converter, wherein the analog filter comprises one or more of a passive filter, an active filter, a low-pass filter, a high-pass filter, a band-pass filter, or a phase-shape filter.

Clause 18: The device of any of the example clauses, further comprising: multiple photodiode circuits, each one being configured to generate a separate one of the plurality of electrical signals responsive to incident light thereon.

Clause 19: The device of any of the example clauses, further comprising a controller circuit configured to receive one or more configuration signals from an external processor via a communication interface, wherein the one or more configuration signals corresponds to either an analog configuration signal or a digital configuration signal.

The device of any of the example clauses, further comprising a processor that is configured to receive the digital signals from the analog-to-digital converter, generate a first image of the eye of the user based on the digital signal at a first time, generate a second image of the eye of the user based on the digital signal at a second time, and determine a direction of gaze or movement of the eye based on a comparison of the first image and the second image.

The above specification, examples and data provide a complete description of the manufacture and use of the composition of the invention. Since many embodiments of the invention can be made without departing from the spirit and scope of the invention, the invention resides in the claims hereinafter appended.

In closing, although the various configurations have been described in language specific to structural features and/or methodological acts, it is to be understood that the subject matter defined in the appended representations is not necessarily limited to the specific features or acts described. Rather, the specific features and acts are disclosed as example forms of implementing the claimed subject matter.

What is claimed is:

1. A device to detect and process light reflected from an eye of a user, the device comprising:
   a first optical detector circuit that provides a first analog detection signal responsive to a first incident light reflected from the eye of the user;
   a second optical detector circuit that provides a second analog detection signal responsive to a second incident light reflected from the eye of the user;
   a first path selector with a first input to receive the first analog detection signal, a second input to receive the second analog detection signal, a control input to receive a first selection signal, and an output to selectively couple one of the first and second inputs to the output responsive to the first selection signal;
   a second path selector with a first input to receive the second analog detection signal, a second input to receive the first analog signal, a control input to receive a second selection signal, and an output to selectively couple one of the first and second inputs to the output responsive to the second selection signal; and
   a summer with a first input that is coupled to the output of the first path selector, a second input that is coupled to the output of the second path selector, and generate a combined analog signal as a summation of the first and second inputs to the summer.

2. The device of claim 1, further comprising: an analog-to-digital converter to receive the combined analog signal, sample the combined analog signals, and generate a digital signal as a conversion of the sampled analog signal into a digital value.

3. The device of claim 2, further comprising a processor that is configured to receive the digital signals from the analog-to-digital converter, generate a first image of the eye of the user based on the digital signal at a first time, generate a second image of the eye of the user based on the digital signal at a second time, and determine a direction of gaze or movement of the eye based on a comparison of the first image and the second image.

4. The device of claim 1, further comprising:
   a first saturation detector to receive the first analog detection signal and generate the first selection signal responsive to a comparison of the first analog detection signal to a first threshold; and
   a second saturation detector to receive the second analog detection signal and generate the second selection signal responsive to a comparison of the second analog detection signal to a second threshold.

5. The device of claim 4, wherein the first and second thresholds are the same.

6. The device of claim 4, wherein the first and second saturation detectors each correspond to a comparator with hysteresis.

7. The device of claim 4, further comprising:
   a first delay circuit that is coupled between the first optical detector circuit and the first and second path selectors, wherein the first delay circuit generates a first delayed analog signal that is delayed in time with respect to the first analog detection signal; and
   a second delay circuit that is coupled between the second optical detector circuit and the first and second path selectors, wherein the second delay circuit generates a second delayed analog signal that is delayed in time with respect to the second analog detection signal.

8. The device of claim 1, further comprising:
   a third optical detector circuit that provides a third analog detection signal responsive to a third incident light reflected from the eye of the user;
   a third path selector with a first input to receive the third analog detection signal, a second input to receive one of the first or second analog detection signals, a control input to receive a third selection signal, and an output to selectively couple one of the first and second inputs to the output responsive to the third selection signal; and
   wherein the summer is further includes a third input that is coupled to the output of the third path selector, wherein the summer generates the combined analog signal as a summation of the first, second, and third inputs to the summer.

9. The device of claim 8, further comprising
   a first saturation detector to receive the first analog detection signal and generate the first selection signal responsive to a comparison of the first analog detection signal to a first threshold;
   a second saturation detector to receive the second analog detection signal and generate the second selection signal responsive to a comparison of the second analog detection signal to a second threshold; and
   a third saturation detector to receive the third analog detection signal and generate the third selection signal responsive to a comparison of the third analog detection signal to a third threshold.

10. The device of claim 1, further comprising: an optical filter that is located between each optical detector circuit and the light incident on the optical detector circuit, wherein the optical filter comprises one or more of: a first filter that selectively blocks wavelengths that are different from an incident beam, a second filter that selectively blocks undesired ambient light, a third filter that selectively blocks light in the red, green, or blue light spectrums, a fourth filter that blocks light in the visible spectrum, a fifth filter that selectively blocks light a wavelength in a specific portion of the infrared wavelength spectrum, or a sixth filter that passes light with a specific polarization.

11. The device of claim 1, further comprising:
an analog filter that filters the combined analog signal prior to generate a filtered signal, wherein the analog filter comprises one or more of a passive filter, an active filter, a low-pass filter, a high-pass filter, a band-pass filter, or a phase-shape filter; and
an analog-to-digital converter that receives the filtered signal and converts the filtered signal to a digital value.

12. A device to detect and process incident light reflected from an eye of a user, the device comprising:
an array of optical detectors, each configured to provide a corresponding one of an array of analog detection signals responsive to a corresponding incident light reflected from the eye of the user;
an array of saturation detectors, each configured to receive the corresponding array of analog detection signal and generate a corresponding selection signal responsive to a comparison of the corresponding analog detection signal to a corresponding threshold; and
a signal combiner configured to receive the plurality of selection signals and the plurality of analog detection signals, wherein the signal combiner is configured to selectively combine the plurality of analog detection signals to generate a combined analog signal based on the array of selection signals, wherein non-saturated signals are promoted over saturated signals in the combined analog signal.

13. The device of claim 12, wherein the signal combiner comprises:
a decoder logic that generates control signals based on the selection signals from the saturation detectors;
a set of multiplexers, where each of the multiplexers receives two different ones of the analog detection signals; and
a summer, wherein the summer is configured to combine the outputs of the set of multiplexers to generate the combined analog signal.

14. The device of claim 13, further comprising:
an analog-to-digital converter to receive the combined analog signal, sample the combined analog signals, and generate a digital signal as a conversion of the sampled analog signal into a digital value; and
a processor that is configured to receive the digital signals from the analog-to-digital converter, generate a first image of the eye of the user based on the digital signal at a first time, generate a second image of the eye of the user based on the digital signal at a second time, and determine a direction of gaze or movement of the eye based on a comparison of the first image and the second image.

15. A device to generate an electrical response to light incident that light includes specular and scattered reflections from the eye of a user, the device comprising:
an optical detector that generates a plurality of electrical signals responsive to the light incident on the optical detector;
a signal combiner that receives the plurality of electrical signals from the optical detector, evaluates a signal level of each of the plurality of electrical signals to determine when the signal level of the corresponding one of the plurality of electrical signals has saturated, and selectively combines the plurality of electrical signals to generate a combined analog signal based on the determined signal levels such that non-saturated signals are promoted over saturated signals in the combined analog signal; and
an analog-to-digital converter that receives the combined analog signal from the signal combiner, samples the combined analog signals, and generates a digital signal as a conversion of the sampled analog signal into a digital value.

16. The device of claim 15, further comprising: an optical filter that is located between the optical detector and the light incident on the optical detector, wherein the optical filter comprises one or more of: a first filter that selectively blocks wavelengths that are different from an incident beam, a second filter that selectively blocks undesired ambient light, a third filter that selectively blocks light in the red, green, or blue light spectrums, a fourth filter that blocks light in the visible spectrum, a fifth filter that selectively blocks light a wavelength in a specific portion of the infrared wavelength spectrum, or a sixth filter that passes light with a specific polarization.

17. The device of claim 15, further comprising: an analog filter that filters the combined analog signal prior to sampling by the analog-to-digital converter, wherein the analog filter comprises one or more of a passive filter, an active filter, a low-pass filter, a high-pass filter, a band-pass filter, or a phase-shape filter.

18. The device of claim 15, the optical detector further comprising: multiple photodiode circuits, each one being configured to generate a separate one of the plurality of electrical signals responsive to incident light thereon.

19. The device of claim 15, further comprising a controller circuit configured to receive one or more configuration signals from an external processor via a communication interface, wherein the one or more configuration signals corresponds to either an analog configuration signal or a digital configuration signal.

20. The device of claim 15, further comprising a processor that is configured to receive the digital signals from the analog-to-digital converter, generate a first image of the eye of the user based on the digital signal at a first time, generate a second image of the eye of the user based on the digital signal at a second time, and determine a direction of gaze or movement of the eye based on a comparison of the first image and the second image.

* * * * *